United States Patent [19]

Büntemeyer et al.

[11] Patent Number: 5,032,524

[45] Date of Patent: Jul. 16, 1991

[54] APPARATUS AND PROCESS FOR THE BUBBLE-FREE GASSING OF LIQUIDS, ESPECIALLY OF CULTURE MEDIA FOR PROPAGATING TISSUE CULTURES

[75] Inventors: Heino Büntemeyer; Jürgen Lehmann, both of Braunschweig, Fed. Rep. of Germany

[73] Assignee: Gesellschaft fur biotechnologische Forschung mbH (GBF), Braunschweig, Fed. Rep. of Germany

[21] Appl. No.: 85,741

[22] PCT Filed: Oct. 2, 1986

[86] PCT No.: PCT/EP86/00566

§ 371 Date: May 18, 1987

§ 102(e) Date: May 18, 1987

[87] PCT Pub. No.: WO87/02054

PCT Pub. Date: Apr. 9, 1987

[30] Foreign Application Priority Data

Oct. 2, 1985 [DE] Fed. Rep. of Germany ....... 3535183

[51] Int. Cl.[5] .......................... C12M 1/06; C12M 1/12

[52] U.S. Cl. ..................................... 435/311; 435/313; 435/316

[58] Field of Search ............... 435/287, 313, 316, 311; 210/500.23

[56] References Cited

U.S. PATENT DOCUMENTS 3,674,440 7/1972 Kitrilakis .............................. 422/48
4,649,114 3/1987 Miltenburger et al. ............. 435/240
4,649,118 3/1987 Anderson ............................ 435/316
4,738,782 4/1988 Yamauchi et al. .................. 210/650

FOREIGN PATENT DOCUMENTS

WO852195 5/1985 World Int. Prop. O. .......... 435/315

Primary Examiner—Allen J. Flanigan
Attorney, Agent, or Firm—Kane, Dalsimer, Sullivan, Kurucz, Levy, Eisele and Richard

[57] ABSTRACT

The invention relates to an apparatus and a process for the bubble-free gassing of liquids, especially of culture media for propagating tissue cultures by means of a porous membrane filament system, whereby liquid media and gas are introduced into the culture. The porous membrane filaments include both hydrophobic and hydrophobic filaments.

4 Claims, 6 Drawing Sheets

APPARATUS AND PROCESS FOR THE BUBBLE-FREE GASSING OF LIQUIDS, ESPECIALLY OF CULTURE MEDIA FOR PROPAGATING TISSUE CULTURES

BACKGROUND OF THE INVENTION

1. Field of the Invention

The invention relates to a further development of apparatus and methods of gassing a liquid and is an improvement over the apparatus and method of German apparatus for bubble-free gassing of culture media.

BRIEF DESCRIPTION OF THE PRIOR ART

To this end, according to the invention an apparatus comprising a membrane sheet provided by means of a membrane cage is provided which is characterised in that the membrane cage is formed from one or more hydrophobic porous hollow membrane filaments.

DETAILED DESCRIPTION OF THE INVENTION

With the hydrophobic porous or microporous hollow membrane filaments provided in accordance with the invention, gassing is effected by way of the membrane pores. The membrane pores are filled with gas so that the gas/liquid phase boundary lies approximately in the pores approximately in the plane of the external face of the hollow membrane filaments, and liquid medium does not enter the hollow membrane filaments. The position of the phase boundary can be adjusted by suitable choice of the pressure in the hollow membrane filaments against the prevailing external pressure.

Apparatus for the bubble-free gassing of liquids, especially of culture media for propagating tissue cultures, are used in reactors that, in addition to the gas supply and removal system, as a rule comprise a system for the cell-free exchange of media. For example, when culturing animal cells in bioreactors the cell-free exchange of media is a problem if cell densities of more than $1 \times 10^7$ cells/ml are to be achieved.

For the continuous cell-free exchange of media, for example spinning filters mounted on a stirrer shaft have been proposed; Develop. biol. Standard, 60 (1985) 229 to 236. As regards the disadvantages that result when tissue cultures are stirred, reference can be made to Patent P 34 30 924.1. External circulation systems with filter units and/or sedimentation paths for microcarrier cultures have also been proposed; Ann. Rep. Ferment. Proc., 6 (1983) 35 to 74. With external circulation systems however, high shearing forces occur as a result of the cell suspensions continuously being pumped around, with the result that the cells are severely damaged. Flat membranes are susceptible to blockage and are also not very satisfactory as regards the throughput of liquid.

To overcome the problems of the State of the Art, the apparatus according to the invention may be provided, in addition, with one or more hydrophilic porous hollow membrane filaments. These hydrophilic porous hollow membrane filaments, together with the hydrophobic porous hollow membrane filame ts, form the membrane cage.

The use of hollow membrane filaments made of polypropylene, for example of polypropylene according to DE-A-31 07 874, has proved advantageous. Porous and microporous hollow membrane filaments made of polypropylene are hydrophobic per se. These hollow membrane filaments can, however, be hydrophilised by being wetted with an organic solvent and then with water. This hydrophilisation can be reversed by drying. The membrane cage can thus be formed from polypropylene hollow membrane filaments, some of which are untreated and some of which have been hyrophilised in a convenient manner.

If liquid medium is alternately introduced into and removed from the reactor by way of the hydrophilic hollow membrane filters, then the hollow membrane filaments are rinsed in an advantageous manner.

In the following the invention is explained in detail by six Figures and four Examples.

Figure 1:
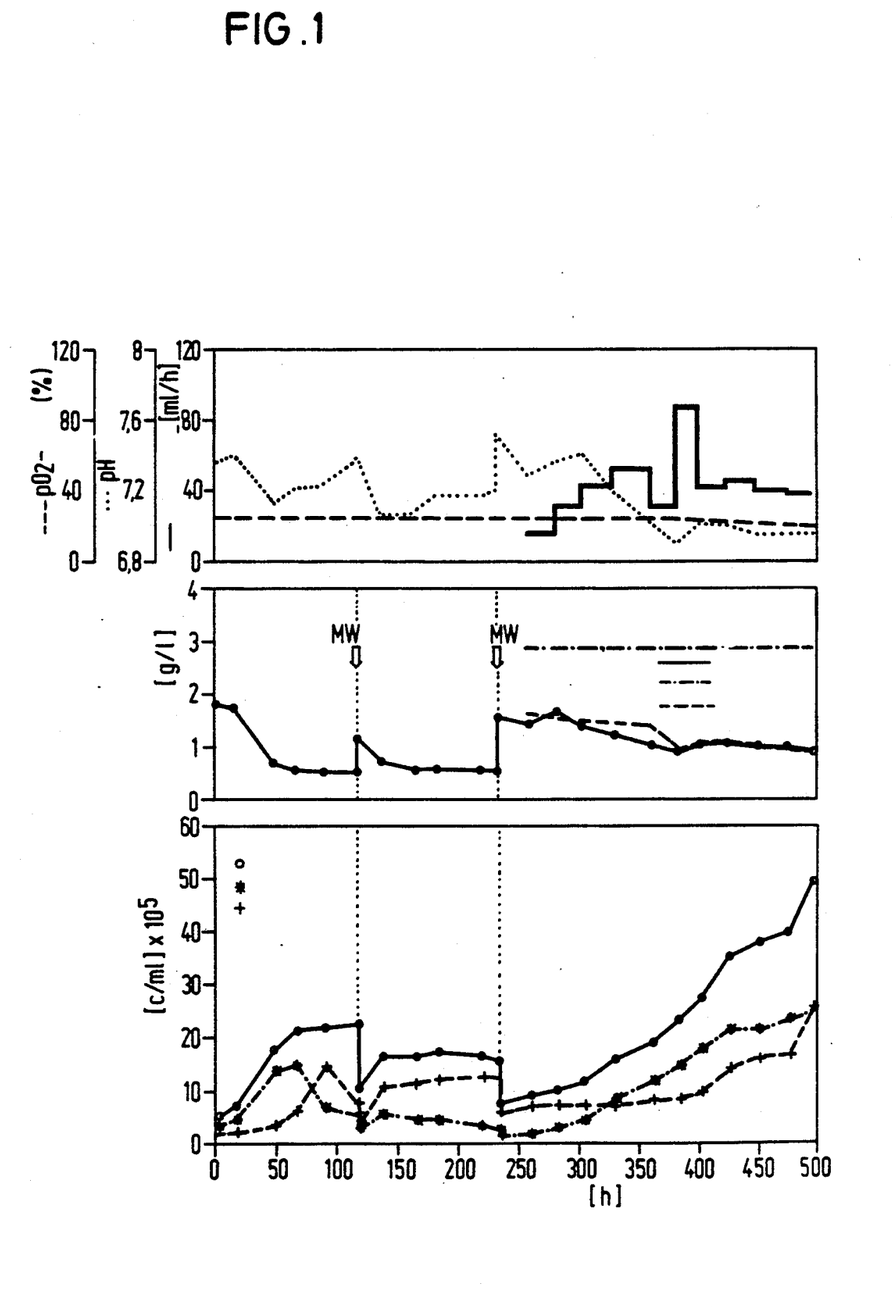
FIGS. 1–3 are graphical representations of fermentations according to the Examples 1–3, respectively.
Figure 2:
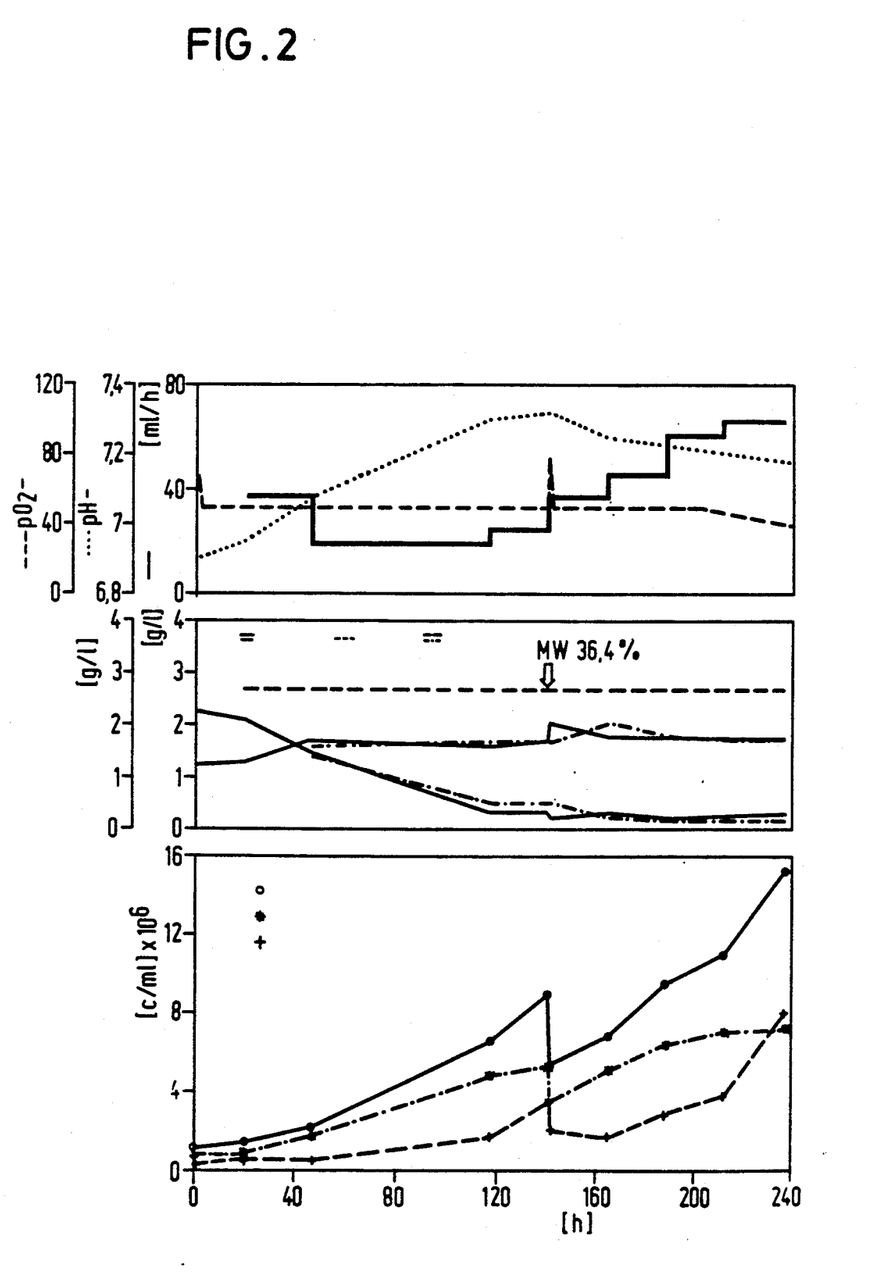
Figure 3:
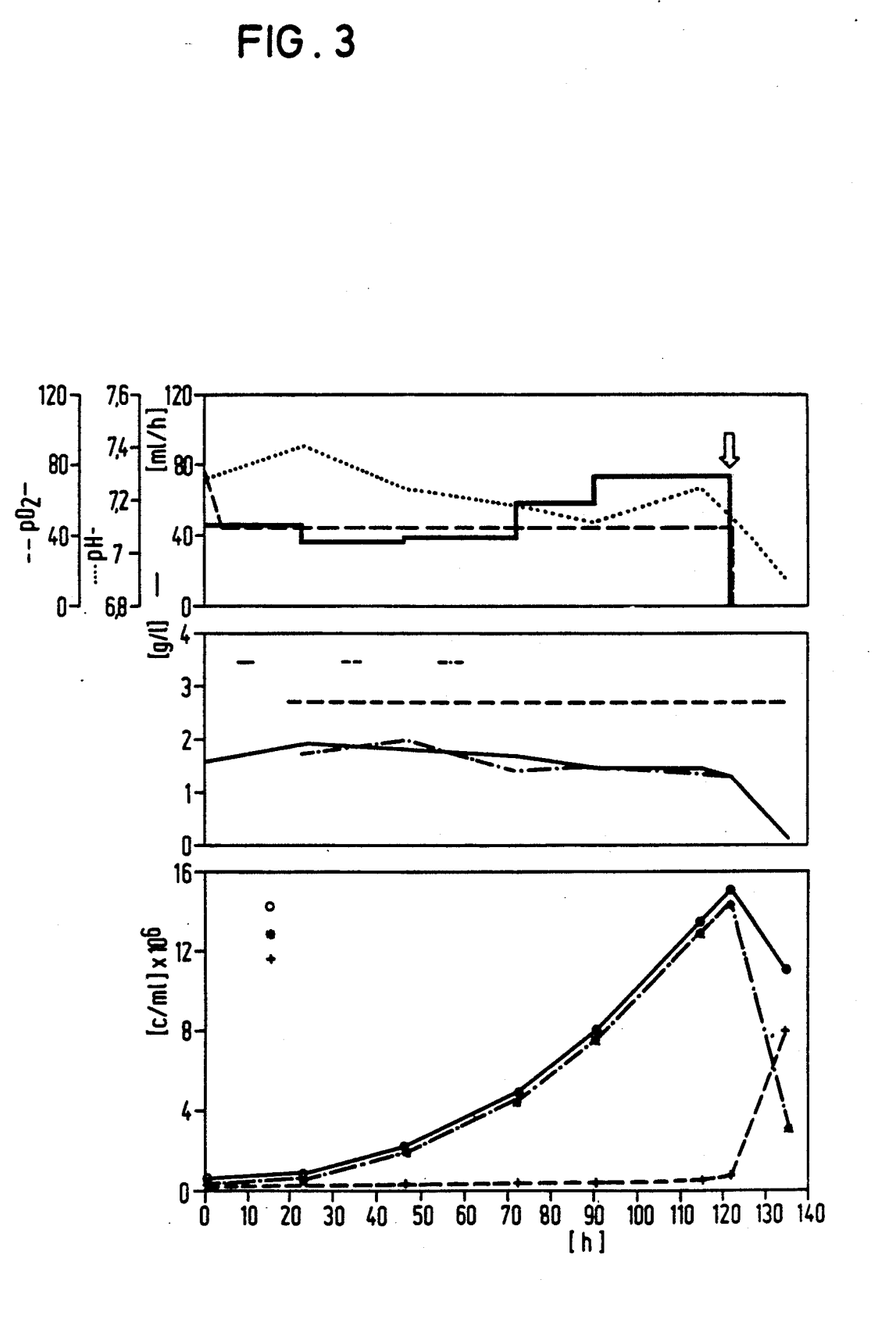
Figure 4:
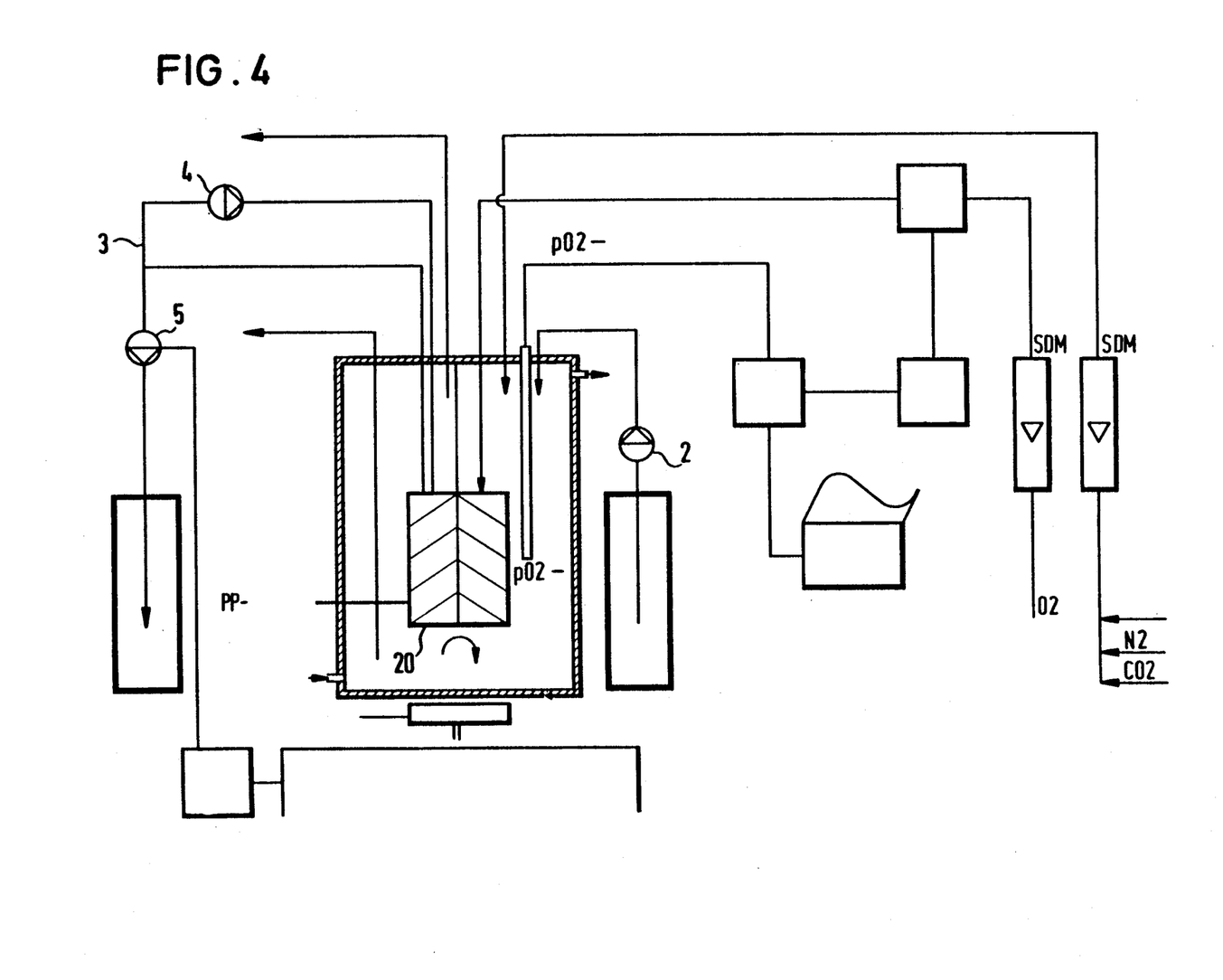
FIG. 4 is a schematic representation of embodiment apparatus used in the Examples 1–3.
Figure 5:
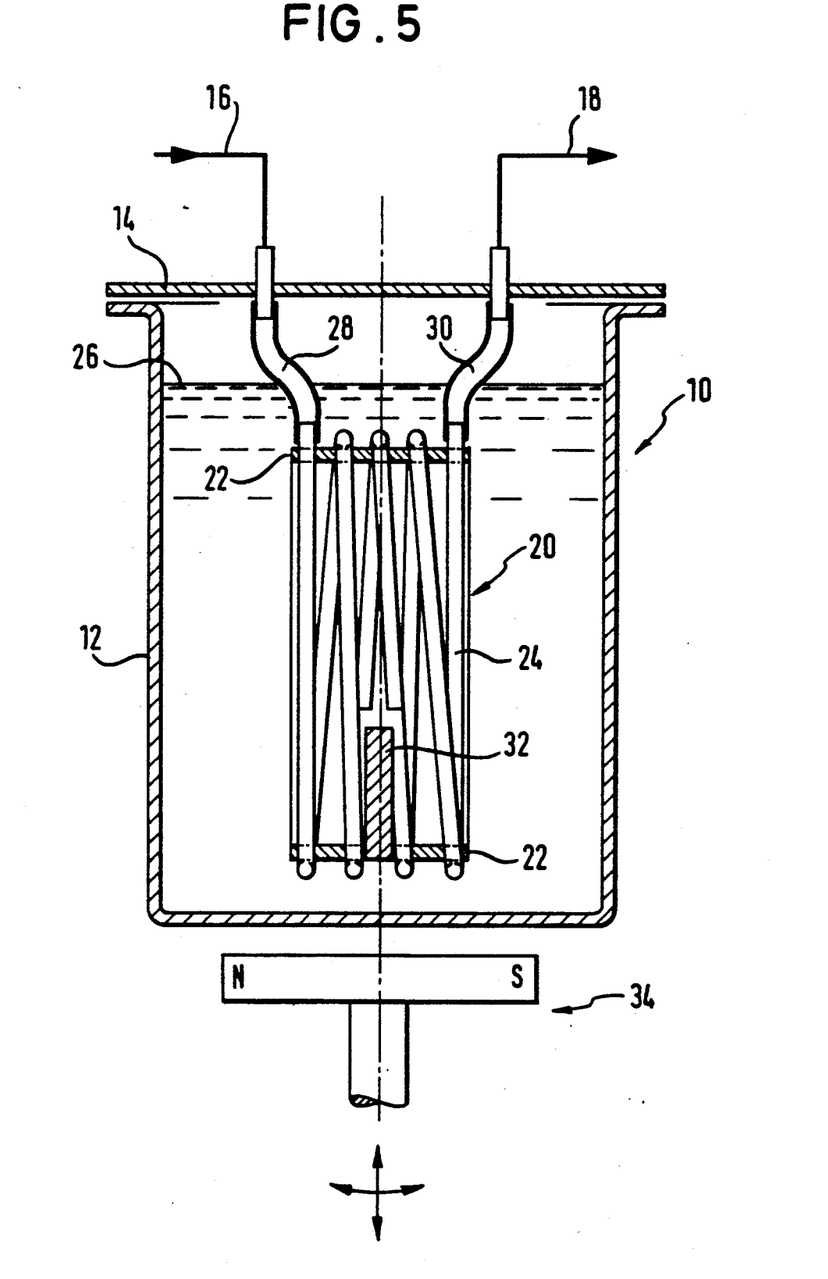
FIGS. 5–6 show fermentation apparatus with membrane cages according to the invention.
Figure 6:
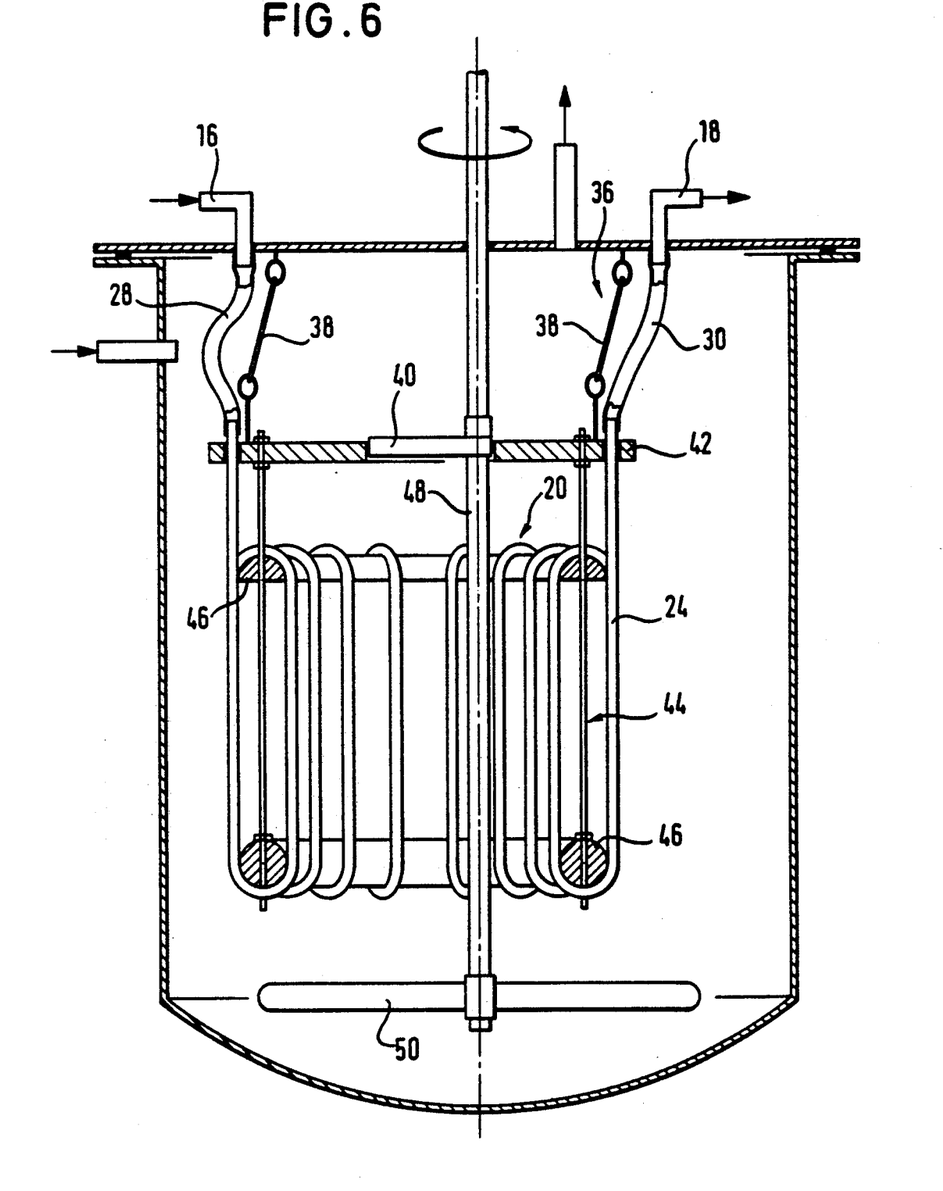

FIGS. 1 to 3 show three fermentations according to Examples 1 to 3,

FIG. 4 shows schematically the apparatus used Examples 1 to 3;

FIGS 5 and 6 show reactors with membrane cages according to the invention having hydrophobic porous hollow membrane filaments.

The schematic construction shown in FIG. 5 of an apparatus 10 according to the invention consists of a non-magnetic vessel 12 on which there is arranged a lid 14 which may optionally be fastened and sealed in a manner not shown. A gas inlet line 16 and a gas outlet line 18 are passed through the lid 14.

There is arranged in the vessel 12 a membrane cage which has a membrane carrier 22 in the shape of a hollow cylinder on which hollow membrane filaments 24 are helically wound. The membrane cage 20 is completely immersed in a body of liquid 26 in the vessel 12 and is flexibly mounted at its upper end by resilient tubes 28 and 30. The tube 28 is connected to the gas inlet line 16 and to one end of the wound hollow membrane filament 24, whilst the tube 30 joins the other end of the wound hollow membrane filament 24 to the gas outlet line 18.

In the lower region of the membrane cage 20 there is attached to the membrane carrier 22, in non-rotatable manner, a magnetic core 32 which can be acted on by a magnet arrangement 34 located outside the vessel 12. In order to impart a pendulum movement to the membrane cage 20, by way of the magnetic core 32, the magnet arrangement 34 can be moved back and forth in a linear movement by way of a device that is not shown. This linear movement is effected in such a direction that the membrane cage 20 moves in pendulum manner about a straight line passing through the points of suspension.

In the lower region of the membrane cage 20 there is attached to the membrane carrier 22, in non-rotatable manner, a magnetic core 32 which can be acted on by a magnet arrangement 34 located outside the vessel 12. In order to impart a circular pendulum movement to the membrane cage 20, by way of the magnetic core 32, the magnet arrangement 34 can be rotated by way of a device that is not shown. With this circular pendulum movement, the membrane cage moves on a circular path without auto-rotation about its axis of symmetry.

Alternatively, it is also possible to initiate a linear movement at a particular angle to the axis of symmetry of the membrane cage in order to superimpose on the linear pendulum movement of the membrane cage, as a result of the resilence of the tubes 28 and 30, an additional component of movement which can result in an elliptical or a circular pendulum movement. It is furthermore also possible to provide, instead of the correspondingly moved magnet arrangement 34, a stationary electromagnet arrangement, the desired pendulum movement or rotary pendulum movement of the membrane cage being achieved by corresponding disposition and actuation of the electromagnets. There is to be understood by "pendulum movement" of the membrane cage a translatory movement, a linear pendulum movement, a circular pendulum movement, a circular swinging movement and combinations of these movement. A rotary movement in one direction about an axis of rotation (without reversal of movement) is not advantageous owing to the shearing action associated therewith.

The gassing rate can be controlled by altering the circular pendulum frequency and/or the radius of the circular path. In the case of the embodiment shown, a corresponding alteration of the circular path radius can be achieved in a simple manner by altering the distance between the gas inlet line 16 and the gas outlet line 18 in the lid 14. For example, by reducing the said distance, the deflection of the membrane cage from the rest position, (that is to say that position in which there is no movement imparted to the membrane cage 20 and the latter remains suspended motionless in the vessel 12) can be correspondingly reduced.

The embodiment shown in FIG. 5 is designed especially for smaller amounts of liquid. For the bubble-free gassing of amounts of liquid of the order of 30 litres or more, according to FIG. 6 the suspension by way of the resilient tubes 28, 30 for the supply and removal of gas is advantageously taken over by a suitable suspension system 36 using flexible or pivotable articulated members (38), and the membrane cage 20, made on a larger scale, is moved with the aid of an eccentric 40. The articulated members 38 can consist, for example, of two or more tension wires of equal length which, spaced from one another, are pivotally mounted on the lid 14 and are hinged to a guide plate 42 which surrounds the eccentric 40 and of which the axis of symmetry coincides with that of the membrane cage 20. This guide plate 42 can be secured by means of a tension ring support 44 to slotted tension rings 46 which, together with the hollow membrane filament or filaments 24, form the correspondingly enlarged membrane cage. To impart a circular pendulum movement to the membrane cage 20, there may be provided a drive shaft 48 engaging in the vessel 12 and, by way of an adjustable eccentric 40, also engaging on or in the guide plate 42. The drive shaft 48 enters preferably through the lid 14 or the base of the vessel 12 in the region of the axis of symmetry of the vessel. If the drive shaft 48 is introduced through the lid 14 of the vessel 12, the guide plate 42 is advantageously arranged above the membrane cage 20, and the shaft 48 can be extended through the hollow cylindrical membrane cage 20 and into the lower half of the vessel 12 and provided at its lower end with a stirrer 50. This stirrer 50 can effect a slow movement of the liquid during the first growing stage of a culture in the so-called initial cultivation phase with a low level of liquid and pure aeration over the surface.

The afore-described apparatus is also suitable as an additional system for conventional fermenters and represents an ideal supplement for existing systems.

Example 1

To investigate the efficiency of the apparatus shown diagrammatically in FIG. 5, a membrane cage 20 was produced on which there had been wound a hydrophobic hollow membrane filament 24 made of Accurel$^R$ type PX 190/1/2/8366 with a pore volume of 75% and a pore size of 0.3 μm. The length of the hollow membrane filament 24 was 121 cm, the outer membrane surface area was 98.7 cm$^2$, and the hollow membrane filament was gassed internally with pure oxygen at a superatmospheric pressure of 30 mm water column. An advantageous membrane material is especially microporous polypropylene, for example Accurel$^R$.

The membrane cage was immersed in 1.3 l of distilled water and moved at a deflection of 2.5 cm around the centre, with 60 circular pendulum movements per minute, by a rotatably mounted magnet arranged beneath the vessel.

Measurements with this apparatus showed that at a temperature of 25° C. an oxygen transfer rate OTR of 56 mg $O_2$/ (1.h) could be achieved without the emergence of oxygen bubbles from the membrane surface. This corresponds to a specific oxygen flow $Q_{O2}$ of 0.57 mg $O_2$/ (cm$^2$.h). In the case of the unmoved surface, using the same apparatus, an oxygen flow $Q_{O2}$ of 0.22 mg $O_2$/(cm$^2$.h) was measured.

The described apparatus is suitable, for example, for the culturing of fibroblasts, for example human diploid foreskin cells (FS-4), which have a specific oxygen requirement $q_{O2}$ of 0.05 mmol $O_2$/($10^9$ cells.h) or 1.6 mg $O_2$/($10^9$ cells.h) It was calculated that with this apparatus 3.5 . $10^{10}$ cells/1 could be supplied.

In the following the use of the process and apparatus is described in another Example. A cell culture with primary human leucocytes with a cell count n of 4.5 . $10^9$ cells/1 and an initial specific oxygen requirement $q_{O2}$ of 4.3 mg $O_2$/($10^9$ cells.h) was treated at 37° C. in a culture medium RPMI 1640 including some process-conditioned additives, using 60 circular pendulum movements per minute at an oxygen super-atmospheric pressure of 30 mm water column. An oxygen transfer rate OTR of 38 mg $O_2$/(1.h) with bubble-free gassing was achieved. This value exceeds the required value by 18.5 mg $O_2$/(1.h). In order to reduce the oxygen transfer rate to the requirement of 19.5 mg $O_2$/(1.h) a simple reduction in the circular pendulum frequency was made.

Control of the oxygen supply as necessary can also be achieved by altering the concentration of gas in the inflowing gas. In the afore-described apparatus, for example a controlled reference value of 10% air saturation was maintained in such a manner that a continuous air flow of 1 Nl/h, with which, if necessary, pure oxygen was admixed, was conveyed through the membrane. The admixing was carried out by means of a magnetic valve controlled by a two-position controller, and the actual value of the air saturation in the medium was measured with an oxygen electrode.

The adjustment of the pH value by way of a buffer-$CO_2$ equilibrium, which is customary in cell culture technology, can be achieved by admixing the required amount of $CO_2$ with the inflowing gas.

The process according to the invention and the apparatus according to the invention are suitable, also in advantageous manner, for the bubble-free gassing of microcarrier cultures.

EXAMPLES 2 to 4

The tubes selected for the hydrophobic and hydrophilic hollow membrane filaments consisted of microporous hydrophobic polypropylene (Accurel$^R$, ENKA AG) and had the following characteristics: $D_i = 1.88$ mm, water column = 0.4 mm, pore size 0.3 μm, external surface area 8.7 cm$^2$/m. For the hydrophilisation, one of the tubes was treated for 1 hour with 70% ethanol and subsequently carefully flushed with pure water (Milli-Q) until free of alcohol.

The two tubes were used in the 1.5 litre scale for three fermentations of a mouse-mouse hybridoma. For this purpose, first the hydrophobic tubular coil according to FIG. 5 and then (in the moist state) the hydrophilic tubular coil 25 are mounted on a magnetically driven pendulum stirrer 20 according to FIG. 5. The respective tube lengths for gassing and media exchange can be seen in FIGS. 1 to 3. As the results show, a ratio of lengths of gassing tube and media exchange tube of 3-4 m/l to 1 m/l for cell densities of about $2 \times 10^7$ cells/ml are advantageous. Neither the hydrophobic nor the hydrophilic tube altered its properties during the vapour sterilisation.

The continuous process was as follows: The supply of fresh medium (nutrients) was carried out freely by way of a metering pump 2. In order to pump off cell-free medium through the hydrophilic tube a circulation system 3 was provided in view of a possible blockage of the pores and in view of the flexibility of the tube. By means of an external pump 4, medium was circulated through the hydrophilic tube. With a further pump 5 it was then possible to remove the corresponding discharge amount from this circulation system 3. In so doing, the discharge flow was no more than half of the circulation flow, so as not to allow the ratio of pore flow to tube internal flow to become too large. Measurements showed that it was possible for at least 150 ml of liquid/h to be removed through 1 m of hydrophilic tube (= times the working volume/d). The fermentation time was 135 h, 240 h and 500 h with different levels of cell density. During these periods no impairment of the efficiency of the hydrophilic tube could be discerned and, as a result, there was no need for any reflushing and regenerating phases.

The results of the three fermentations are shown in FIGS. 1 to 3.

FIG. 1 shows the behaviour of a batch culture (Example 2) with subsequent continuous culture with cell retention. The fermentation conditions were as follows:
Cell line: FIB MONO 6
Medium: ISCOVE'S DMEM, HAM'S F12 1:1
Additives: 2 mM glutamine, 6.25 ug/l gentamycin
Serum: 2% (V/V) FCS
Reactor: volume: 1.5 litres, working volume: 1.2 litres
Gassing: 2 m hydrophobic polypropylene tube
Medium exchange: 2 m hydrophilic polypropylene tube The maximum living cell density of the batch culture was approximately $1.5 \times 10^6$ cells/ml, a value typical also for other fermentations. With the aid of cell retention it was possible in this Example to achieve a living cell density of approximately $2.5 \times 10^6$ cells/ml. As a result of the high proportion of dead lysed cells and their disturbing effect at the beginning of the continuous part ($t_F = 235$ h) it was not possible to achieve an even higher cell density.

FIG. 2 shows the results of a second fermentation (Example 3) with the same cell line. The fermentation conditions were as follows:
Cell line: FIB MONO 6
Medium: ISCOVE'S DMEM, HAM'S F12 1:1
Additives: 2 mM glutamine, 6.25 ug/l gentamycin
Serum: 4% (V/V) FCS
Reactor: volume: 1.5 litres, working volume: 1.2 litres
Gassing: 2 m hydrophobic polypropylene tube
Medium exchange: 2 m hydrophilic polypropylene tube. In this test inoculation with a high cell density (living cell density $8 \times 10^5$ cells/ml) was effected and the continuous process was begun after 24 hours. Within a period of 240 hours a living cell density of $7.2 \times 10^6$ cells/ml could be achieved in spite of a single removal of 36% of the cell mass. The oxygen supply to the cells was increasingly problematic.

In FIG. 3 the results of the third fermentation (Example 4) with the same cell line are shown. The fermentation conditions were as follows:
Cell line: FIB MONO 6
Medium: ISCOVE'S DMEM, HAM'S F12 1:1
Additives: 2 mM glutamine, 6.25 ug/l gentamycin
Serum: 1% (V/V) FCS
Reactor: volume: 1.5 litres, working volume: 1.2 litres
Gassing: 2.8 m hydrophobic polypropylene tube
Medium exchange: 1 m hydrophilic polypropylene tube. This time inoculation was carried out with a lower cell density (living cell density $3.5 \times 10^5$), but the continuous process was started immediately. After only 120 hours a living cell density of $1.5 \times 10^7$ cells/ml was achieved. With this cell density the supply of oxygen (2.8 m tube) could still be guaranteed.

The results of the three fermentations demonstrate clearly that at least 100 ml of medium per metre of tube per hour could be removed from the reactor, which corresponded to the supply of approximately $2 \times 10^7$ cells/ml. There were no problems regarding the efficiency of the tube (blockage, collapse).

We claim:

1. In apparatus for the bubble-free gassing of liquids, with a gas exchange across an immersed membrane sheet provided by means of a membrane cage which is movable in the manner of a pendulum, the improvement, which comprises; said membrane cage comprising one or more hydrophobic porous hollow membrane filaments as the immersed membrane sheet and one or more hydrophilic porous hollow membrane filaments as means for nutrient exchange.

2. Apparatus according to claim 1, wherein
   porous polypropylene hollow membrane filaments are used as hydrophobic hollow membrane filaments and
   porous polypropylene hollow membrane filaments are used as hydrophilic hollow membrane filaments, obtainable by hydrophilisation of porous polypropylene hollow membrane filaments by wetting with an organic solvent and subsequent wetting with water.

3. Process for the bubble-free gassing of liquid culture media for propagating tissue cultures, which comprises;
   A. providing a reactor, which comprises;
      (i) a vessel for containing the liquid culture media;
      (ii) a membrane cage adapted by size and configuration to nest within the vessel, immersed in the liquid culture medium contained therein;

said cage being mounted so as to be movable in a pendulum movement;

said cage being composed of one or more hydrophobic, porous, hollow membrane filaments and one or more hydrophilic, porous, hollow membrane filaments;

B. providing a liquid culture medium in the vessel;

C. immersing the membrane cage in the culture medium in the vessel;

D. introducing a gas into the culture medium through the hydrophobic porous hollow membrane filaments; and E. exchanging fresh nutrient for old nutrient through the hydrophilic porous, hollow membrane filaments.

4. Process according to claim 3, characterised in that liquid medium is introduced intermittently into the reactor, and liquid medium is removed from the reactor, by way of the hydrophilic porous hollow membrane filaments.

* * * * *

UNITED STATES PATENT AND TRADEMARK OFFICE
CERTIFICATE OF CORRECTION

PATENT NO. : 5,032,524
DATED : July 16, 1991
INVENTOR(S) : Heino Buntemeyer and Jurgen Lehmann It is certified that error appears in the above-identified patent and that said Letters Patent is hereby corrected as shown below:

Col. 1, line 14; After the heading BRIEF DESCRIPTION OF THE PRIOR ART insert the following paragraph and heading -- It has become apparent that the process described in German Patent P 34 30 924.1 with the apparatus described therein having porous or microporous hollow membrane filaments made of any desired plastics material can be carried out in an advantageous manner if the hollow membrane filaments are hydrophobic.

UNITED STATES PATENT AND TRADEMARK OFFICE
CERTIFICATE OF CORRECTION

PATENT NO. : 5,032,524

DATED : July 16, 1991

INVENTOR(S) : Heino Buntemeyer, et al

It is certified that error appears in the above-identified patent and that said Letters Patent is hereby corrected as shown below:

Col. 4, line 39; "n" should read -- $\underline{n}$ -- .

Col. 5, line 42; (= times ) should read -- ($\hat{=}$ three times) -- .

Signed and Sealed this

Twenty-second Day of December, 1992

Attest:

DOUGLAS B. COMER

*Attesting Officer*    Acting Commissioner of Patents and Trademarks